United States Patent [19]
Achilefu

[11] Patent Number: 6,013,243
[45] Date of Patent: Jan. 11, 2000

[54] GASEOUS INHALABLE ULTRASOUND CONTRAST AGENTS AND METHOD THEREFOR

[75] Inventor: Samuel I. A. Achilefu, St. Louis, Mo.

[73] Assignee: Mallinckrodt Inc., St. Louis, Mo.

[21] Appl. No.: 08/944,714

[22] Filed: Oct. 6, 1997

Related U.S. Application Data

[63] Continuation of application No. 08/486,629, Jun. 7, 1995, abandoned.

[51] Int. Cl.⁷ ................................................. A61K 49/04
[52] U.S. Cl. ............................................. 424/9.52; 424/9.5
[58] Field of Search ..................... 424/9.5, 9.51, 424/9.52; 600/458, 441

[56] References Cited

U.S. PATENT DOCUMENTS

| | | | |
|---|---|---|---|
| 4,769,241 | 9/1988 | Heldebrant et al. | 424/161 |
| 5,264,220 | 11/1993 | Long, Jr. et al. | 424/450 |
| 5,397,562 | 3/1995 | Mason et al. | 424/9.3 |
| 5,406,950 | 4/1995 | Brandenburger et al. | 128/662.02 |
| 5,417,742 | 5/1995 | Tamhankar et al. | 95/96 |
| 5,705,187 | 1/1998 | Unger | 424/450 |

FOREIGN PATENT DOCUMENTS 9306869  4/1993  WIPO ........................... A61K 49/00

*Primary Examiner*—Jose' G. Dees
*Assistant Examiner*—Michael G. Hartley
*Attorney, Agent, or Firm*—Lawrence L. Limpus

[57] ABSTRACT

Inhalable ultrasound contrast imaging agents that are capable of forming microbubbles in vivo after administration to a patient are provided. The imaging agent is comprised of a gaseous mixture of an insoluble perfluorocarbon gas and at least about 20% oxygen by volume that is administered by a standard inhalation apparatus. Carbogen may be mixed with the insoluble perfluorocarbon gas in an amount sufficient to provide 20% oxygen by volume in the final gaseous mixture. A method of ultrasound imaging an individual by administering the gaseous composition of the invention to an individual by an inhalation apparatus and then subjecting the individual to an ultrasound scan is also provided.

28 Claims, No Drawings

GASEOUS INHALABLE ULTRASOUND CONTRAST AGENTS AND METHOD THEREFOR

This is a continuation of Ser. No. 08/486,629 filed on Jun. 7, 1995, abandoned.

FIELD OF THE INVENTION

This invention relates in general to ultrasound contrast imaging agents, and more particularly to an inhalable imaging agent and method of imaging that utilizes an insoluble perfluorocarbon gas.

BACKGROUND OF THE INVENTION

The discovery of suitable ultrasound contrast imaging agents for human diagnostic applications has been the focus of considerable research and development in recent years. This research has yielded several potential ultrasound contrast imaging agents such as gas-filled microbubbles encapsulated with denatured albumin as described in U.S. Pat. Nos. 4,572,203, 4,718,433, 4,774,958, and 4,844,882 which have issued to Feinstein and Molecular Biosystems, Inc.; gas-filled microbubbles encapsulated by liposomes as described in U.S. Pat. Nos. 5,088,499 and 5,123,414 which have issued to Unger; gas-filled, free microbubbles as described in U.S. Pat. Nos. 5,393,524, and 5,409,688 which have issued to Sonus Pharmaceuticals, Inc.; and saccharide containing solid particles that are mixed with a diluent to produce an ultrasound contrast agent as described in U.S. Pat. Nos. 4,442,843 and 4,681,119, both assigned to Schering AG.

Even though each of these compositions is unique in its basic physical characteristics, each is provided in the form of an aqueous medium or suspension that is to be administered by intravenous infusion to the patient. This is a significant disadvantage to the clinical use of these agents because it introduces additional variables, such as injection rate and volume to be administered, that could adversely impact the efficacy of the agent. In some instances, large volumes of the contrast agent may be required which is undesirable from a patient comfort perspective and is preferably avoided. Moreover, one of the inherent advantages of the use of ultrasound as the imaging modality is the non-invasive nature of the application. When a contrast imaging agent is administered intravenously, the non-invasive advantage presented by this modality is diminished and a decision must be made as to whether the diagnostic procedure warrants the added cost and delays associated with intravenous infusion. This is particularly important when an ultrasound is to be conducted in connection with a cardiac stress test.

An inhalable gaseous ultrasound imaging agent was described in PCT International publication number WO 93/06869 that comprised a gas or mixture of gases that were capable of forming bubbles after administration to a patient. As disclosed therein, the gaseous compositions that were believed to be suitable were those that were poorly soluble in oil, but somewhat more soluble in water. More specifically, WO 93/06869 disclosed that those gases with very low oil:gas partition coefficients, less than about 0.1 would be less effective than those with higher oil:gas partition coefficients and stated that preferred suitable compounds would be compounds described as weak or poor anesthetic agents, e.g., nitrous oxide, xenon, ethylene, sulfur hexafluoride and argon. Unfortunately, none of the compounds described in WO 93/06869 have ultimately been shown to have any utility as ultrasound contrast agents as they have failed to form bubbles in vivo. The search for an inhalable contrast imaging agent continues, however, because of the considerable potential associated with the use of an inhalable gas as an ultrasound contrast imaging agent. An inhalable agent would not require intravenous infusion, would be easily administered and not require large dosage volumes, and could readily be administered without concern for substantial added cost, delays or additional invasiveness.

Perfluorocarbons are currently used in biomedical applications including blood substitutes, imaging agents and liquid ventilation media. Many perfluorocarbon derivatives are used as anesthetic agents that are somewhat resistant to biotransformation. They are partially fluorinated and readily dissolve in blood on passage from the lung alveoli. This solubility factor significantly limits their use as ultrasound contrast agents. Perfluorocarbons are insoluble in blood and intravenous injection of the neat perfluorocarbon liquid is likely to cause liquid embolism and instant death.

A need exists, therefore, for a gaseous ultrasound contrast imaging agent that can be inhaled by a patient and that is capable of providing contrast after administration.

SUMMARY OF THE INVENTION

The present invention is directed to inhalable ultrasound contrast imaging agents that are capable of forming microbubbles in vivo after administration to a patient. The imaging agent is comprised of a gaseous mixture of an insoluble perfluorocarbon gas and at least about 20% oxygen by volume that is administered by a standard inhalation apparatus. In a preferred embodiment, carbogen is mixed with the insoluble perfluorocarbon gas in an amount sufficient to provide 20% oxygen by volume in the final gaseous mixture. The invention is further directed to a method of ultrasound imaging an individual by administering the gaseous composition of the invention to an individual by an inhalation apparatus and then subjecting the individual to an ultrasound scan.

Among the many advantages of the present invention may be found the provision of a contrast agent for ultrasound applications that can be administered quickly, conveniently and in a non-invasive manner; a contrast agent for ultrasound applications that does not require large dosage volumes; a contrast agent for ultrasound applications that can be readily prepared in a physiologically acceptable purity in a cost-effective manner; a contrast agent for ultrasound applications that can be administered to individuals who are in less than optimal physical condition; and the provision of a mixture of gases that forms microbubbles in vivo which permits an image by ultrasound to be obtained.

DETAILED DESCRIPTION OF THE PREFERRED EMBODIMENTS

It has been discovered that a gaseous mixture of an insoluble perfluorocarbon gas and at least about 20% oxygen by volume is a suitable inhalable composition for ultrasound contrast imaging. As used herein, an insoluble perfluorocarbon gas is a gas that is neither water nor lipid soluble in terms of having an oil:gas partition coefficient of less than or equal to about 0.01 and is a gas at 37° C. Examples of suitable perfluorocarbon gases include perfluoroethane, perfluoropropane, octafluorocyclobutane, perfluorocyclobutene, perfluorodimethylamine, perfluoroethylamine, perfluoropentane, perfluoropentene, perfluoroethylene, perfluorotetrahydrofuran, perfluorodiethyl ether, perfluoroethyl methyl ether, perfluoroneopentane, perfluorooxalene, perfluorooxane, perfluorooxetane, perfluoromethane and perfluoropropylene. In a preferred embodiment the insoluble perfluorocarbon gas is perfluoroethane.

The insoluble perfluorocarbon gas may be mixed with another gas such as air, nitrogen, oxygen, carbon dioxide, or a mixture of these gases such as Carbogen which is a mixture of 95% oxygen and 5% carbon dioxide. In practice, the composition to be administered to an individual to be imaged should contain at least about 20% oxygen by volume to ensure proper oxygenation of the individual and to avoid hypoxia. Thus, if a mixture of gases is to be added to the insoluble perfluorocarbon gas, it should be added in an amount sufficient to provide at least about 20% oxygen by final volume. The gas mixtures are prepared according to the art using gases available from the fractionation of air and those prepared synthetically.

Examples of suitable gas mixtures useful in accordance with the invention described herein include: 79% perfluoroethane and 21% Carbogen; 80% perfluoroethane and 20% oxygen; 70% perfluoroethane, 20% oxygen and 10% nitrogen; and 79% octafluoropropane and 21% Carbogen.

Both the insoluble perfluorocarbon gas and the mixing gas containing the oxygen component of the gaseous mixture must be biocompatible and of a physiologically acceptable purity. The gases or gas mixture may be sterilized prior to administration or administered through a sterilizing filter. The gas or gas mixture is administered to an individual by means of a standard inhalation apparatus which is known in the art. The gaseous mixture is typically administered for between about 30 seconds and 10 minutes, and more preferably for about 1–2 minutes although longer or shorter periods of administration may be necessary or preferred for particular clinical applications or patient conditions.

Although not intending to be bound by the following mechanism, it is believed that the mixture of a perfluorocarbon gas and a mixing gas as described above forms microbubbles of perfluorocarbon gas in vivo. Administration of the gas mixture by inhalation allows it to diffuse through lung alveoli into the blood. While the mixing gases undergo their normal physiological processes in the blood, the insoluble perfluorocarbon gas will generate microbubbles in vivo because of their unique properties including lower solubility, and higher density and vapor pressure than the other components of the gaseous mixture. In effect, the mixing gas acts as a solvent during pulmonary delivery and facilitates the "precipitation" of the insoluble perfluorocarbon gas in blood. The perfluorocarbon gas may form micelles with surfactants endogenous in the blood, such as globular proteins, with the perfluorocarbon gas trapped within the hydrophobic shells. As a result, the perfluorocarbon gas bubbles may be carried throughout the vascular system as small gas pockets.

After administration of the inhalable gaseous mixture to an individual, an ultrasound scan is performed using an ultrasound machine known and available in the art. A period of time sufficient for the inhaled gas mixture to generate bubbles in vivo is given before the ultrasound image may be obtained. Depending upon the tissue or organ to be imaged, additional time must be permitted for the bubbles to be carried to the desired tissue or organ before it can be imaged.

The following examples describe preferred embodiments of the invention. Other embodiments within the scope of the claims herein will be apparent to one skilled in the art from consideration of the specification or practice of the invention as disclosed herein. It is intended that the specification, taken together with the examples, be considered exemplary only, with the scope and spirit of the invention being indicated by the claims.

EXAMPLE 1

A gaseous mixture of 79% perfluoroethane and 21% Carbogen in a 20 mL syringe is connected to the flanged adaptor on the inlet tubing of a CMA/10 microdialysis probe (BAS Bioanalytical Systems, Inc.). A syringe is then placed on a Harvard Apparatus Pump 44. The microdialysis probe is placed in a 50 mL soft plastic beaker filled with 5% Human Serum Albumin (HSA) that is osmotically equivalent to blood plasma. The tip of the stainless steel cannula of the microdialysis probe is placed in the HSA so that it is perpendicular to the ultrasound probe. The interface between the beaker and the ultrasound probe is filled with Aquasonic 100 which is a water soluble contact medium for ultrasound transmission (Parker Laboratories, Inc.). The outlet tubing of the microdialysis probe is immersed in another 50 mL beaker containing distilled water which generates a small back pressure on the dialysis probe. Using the Harvard Apparatus Pump, the flow rate of the gas or gas mixture is set at 0.5 mL per minute. The gas mixture enters the probe through the inner stainless steel tube where it contacts the dialysis membrane and then flows through the outer stainless steel tube and exits the microdialysis probe. The dialysis membrane mimics the lungs and a fraction of the gas mixture diffuses through it and exits the tip of the cannula into the HSA. Bubbles generated are immediately detected by the ultrasound probe. The soluble gases in the mixture, oxygen and carbon dioxide, readily dissolve in the HSA solution and do not generate stable bubbles. The insoluble gas perfluoroethane (PFE) is readily encapsulated by the HSA and encapsulated PFE bubbles float to the top of the solution.

EXAMPLE 2

This example is similar to that described in Example 1 except that a Hollow Fiber Model Membrane Oxygenator (HF-500 from C. R. Bard, Inc.) is used in place of the dialysis probe. This oxygenator is specifically designed to mimic human lungs. Plasma is circulated by a peristaltic pump over a network of hollow fibers. A gaseous mixture of 80% PFE and 20% oxygen is circulated inside the hollow fiber bed. An ultrasound probe is placed perpendicular to the outlet tube of the plasma. The results are similar to those described above.

EXAMPLE 3

This example describes a method of administration of a gaseous mixture of this invention.

A dog is laid with its back to a table and an ultrasound probe is placed perpendicular to its body so as to image the left ventricle. The dog is allowed to breathe a gas mixture containing at least 18% oxygen and 40% perfluorocarbon from a mask. The contrast of the left ventricle is enhanced as the gas bubbles pass through it. Once this enhancement reaches a desired optimal value, the mask is removed and the animal is allowed to breath normal air.

This procedure can be used for whole body imaging. It should be noted that the bubbles of this invention can be readily re-inflated as oxygen diffuses into it when it passes through the lungs.

What is claimed is:

1. An inhalable composition for ultrasound contrast imaging comprising: an inhalable gaseous mixture of an insoluble perfluorocarbon gas that is neither water nor lipid soluble on terms of having an oil:gas partition coefficient of less than 0.01 and carbogen sufficient to provide at least about 20% oxygen by volume.

2. The inhalable composition of claim 1 wherein the perfluorocarbon gas is selected from the group consisting of perfluoroethane, perfluoropropane, octafluorocyclobutane, perfluorocyclobutene, perfluorodimethylamine, perfluoroethylamine, perfluoropentane, perfluoropentene, perfluoroethylene, perfluorotetrahydrofuran, perfluoromethane and perfluoropropylene.

3. The inhalable composition of claim 2 wherein the perfluorocarbon gas is perfluoroethane.

4. The inhalable composition of claim 2 wherein the perfluorocarbon gas is perfluoropropane.

5. The inhalable composition of claim 2 wherein the perfluorocarbon gas is octafluorocyclobutane.

6. The inhalable composition of claim 2 wherein the perfluorocarbon gas is perfluorocyclobutene.

7. The inhalable composition of claim 2 wherein the perfluorocarbon gas is perfluorodimethylamine.

8. The inhalable composition of claim 2 wherein the perfluorocarbon gas is perfluoroethylamine.

9. The inhalable composition of claim 2 wherein the perfluorocarbon gas is perfluoropentane.

10. The inhalable composition of claim 2 wherein the perfluorocarbon gas is perfluoropentene.

11. The inhalable composition of claim 2 wherein the perfluorocarbon gas is perfluoroethylene.

12. The inhalable composition of claim 2 wherein the perfluorocarbon gas is perfluorotetrahydrofuran.

13. The inhalable composition of claim 2 wherein the perfluorocarbon gas is perfluoromethane.

14. The inhalable composition of claim 2 wherein the perfluorocarbon gas is and perfluoropropylene.

15. A method for performing ultrasound imaging of an individual comprising: administering an inhalable pharmaceutically acceptable mixture of gases in an ultrasound diagnostically effective amount to the individual, the gaseous mixture comprised of an insoluble perfluorocarbon gas that is neither water nor lipid soluble on terms of having an oil:gas partition coefficient of less than 0.01 and carbogen sufficient to provide at least about 20% oxygen by volume; and subjecting the individual to an ultrasound scan.

16. The method of claim 15 wherein the perfluorocarbon gas is selected from the group consisting of perfluoroethane, perfluoropropane, octafluorocyclobutane, perfluorocyclobutene, perfluorodimethylamine, perfluoroethylamine, perfluoropentane, perfluoropentene, perfluoroethylene, perfluorotetrahydrofuran, perfluoromethane and perfluoropropylene.

17. The method of claim 16 wherein the perfluorocarbon gas is perfluoroethane.

18. The method of claim 16 wherein the perfluorocarbon gas is perfluoropropane.

19. The method of claim 16 wherein the perfluorocarbon gas is octafluorocyclobutane.

20. The method of claim 16 wherein the perfluorocarbon gas is perfluorocyclobutene.

21. The method of claim 16 wherein the perfluorocarbon gas is perfluorodimethylamine.

22. The method of claim 16 wherein the perfluorocarbon gas is perfluoroethylamine.

23. The method of claim 16 wherein the perfluorocarbon gas is perfluoropentane.

24. The method of claim 16 wherein the perfluorocarbon gas is perfluoropentene.

25. The method of claim 16 wherein the perfluorocarbon gas is perfluoroethylene.

26. The method of claim 16 wherein the perfluorocarbon gas is perfluorotetrahydrofuran.

27. The method of claim 16 wherein the perfluorocarbon gas is perfluoromethane.

28. The method of claim 16 wherein the perfluorocarbon gas is and perfluoropropylene.

* * * * *